US008481262B2

(12) United States Patent
Schmidt et al.

(10) Patent No.: US 8,481,262 B2
(45) Date of Patent: *Jul. 9, 2013

(54) METHOD FOR ENRICHING AND/OR SEPARATING PROKARYOTIC DNA USING A PROTEIN THAT SPECIFICALLY BONDS TO UNMETHYLATED DNA CONTAINING CPG-MOTIFS

(75) Inventors: Karl-Hermann Schmidt, Stadtroda (DE); Eberhard Straube, Jena (DE); Stefan Russwurm, Jena (DE); Hans-Peter Deigner, Lampertheim (DE); Svea Sachse, Jena (DE); Marc Lehmann, Jena (DE)

(73) Assignee: SIRS-Lab GmbH, Jena (DE)

( * ) Notice: Subject to any disclaimer, the term of this patent is extended or adjusted under 35 U.S.C. 154(b) by 1324 days.

This patent is subject to a terminal disclaimer.

(21) Appl. No.: 10/591,633

(22) PCT Filed: Mar. 2, 2005

(86) PCT No.: PCT/EP2005/002198
§ 371 (c)(1),
(2), (4) Date: Jul. 17, 2007

(87) PCT Pub. No.: WO2005/085440
PCT Pub. Date: Sep. 15, 2005

(65) Prior Publication Data
US 2008/0003568 A1 Jan. 3, 2008

(30) Foreign Application Priority Data
Mar. 5, 2004 (DE) .......................... 10 2004 010 928
Jan. 14, 2005 (DE) .......................... 10 2005 001 889

(51) Int. Cl.
*C12Q 1/68* (2006.01)
*C07H 21/04* (2006.01)
*C07K 14/00* (2006.01)

(52) U.S. Cl.
USPC .......................... 435/6.12; 536/23.1; 530/350

(58) Field of Classification Search
USPC ............................... 435/6; 530/350
See application file for complete search history.

(56) References Cited

U.S. PATENT DOCUMENTS

| | | | | |
|---|---|---|---|---|
| 5,817,290 A * | 10/1998 | Vijg et al. | ....................... | 424/9.2 |
| 6,239,116 B1 | 5/2001 | Krieg et al. | | |
| 7,507,872 B2 | 3/2009 | Akira et al. | | |
| 8,062,854 B2 * | 11/2011 | Schmidt et al. | .............. | 435/7.21 |
| 8,288,115 B2 * | 10/2012 | Schmidt et al. | .............. | 435/7.21 |
| 2003/0124655 A1 | 7/2003 | Akira et al. | | |
| 2007/0068870 A1 * | 3/2007 | Johnson et al. | ............... | 210/645 |
| 2008/0076671 A1 * | 3/2008 | Bird et al. | ......................... | 506/9 |
| 2010/0316993 A1 | 12/2010 | Schmidt et al. | | |

FOREIGN PATENT DOCUMENTS

| | | |
|---|---|---|
| CA | 2385302 A1 * | 2/2002 |
| CA | 2498951 A1 | 4/2004 |
| CA | 2385302 | 8/2009 |
| JP | 2002-034565 | 2/2002 |
| WO | WO 01/12659 A2 * | 2/2001 |
| WO | WO 02/06482 | 1/2002 |

OTHER PUBLICATIONS

Cross SH. Purification of CpG islands using a methylated DNA binding column. Nature Genetics, vol. 6, No. 3, pp. 236-244, 1994.*
Stacey, et al., The Molecular Basis for the Lack of Immunostimulatory Activity of Vertebrate DNA, The Journal of Immunology, 70:3614-3620 (2003).
Rothenfuber, et al., CpG-Oligonukleotide: Immuntherapie nach dem Muster bakterieller DNA, Deutsches Arzteblatt 98, Heft 15 vom Apr. 13, 2001, pp. A981-A985 (2001).
S. Sachse, et al., "Using a DNA-binding protein to enrich prokaryotic DNA from a mixture of both, eukaryotic and prokaryotic DNA," 56, DGHM-JAHRESTAGUNG, XP002332325 (Sep. 29, 2004).
Cross, et al., "Purification of CpG islands using a methylated DNA binding column," *Nature Genetics*, vol. 6, No. 3, pp. 236-244 (Mar. 1, 1994).
Voo, et al., "Cloning of a Mammalian Transcriptional Activator That Binds Unmethylated CpG Motifs and Shares a CXXC Domain with DNA Methyltrasferase, Human Trithorax, and Methyl-CpG Binding Domain Protein 1," *Molecular and Cellular Biology*, vol. 20, No. 6, pp. 2108-2121 (Mar. 2000).
NCBI Sequence Database, AAF37799.
International Journal of Medical Microbiology, 294S1, p. 181, 56. Jahrestagung der DGHM (Sep. 26-29, 2004).
Clinical Microbiology and Infection, 15th European Congress of Clinical Microbiology and Infectious Diseases, vol. 11, Supplement 2, p. 67 (Apr. 2-5, 2005).
Chinese Office Action for Chinese Application No. 03822233.7, date stamped Sep. 26, 2008.8 pages.
English Translation of Chinese Office Action for Chinese Application No. 03822233.7, 8 pages.
Sequence from GenBank Accession No. AB045180 created Dec. 13, 2000. 3 pages.
Hacker, Georg, Redecker, Vanessa, and Hacker, Hans. (2002) Activation of the Immune System by Bacterial CpG-DNA. Immunology 105:245-251.
Carlone et al., "Cloning and characterization of the gene encoding the mouse homologue of CpG binding protein," Gene: An International Journal on Genes and Genomes, Elsevier Science Publishers, Barking, GB, vol. 295, No. 1, Jul. 24, 2002, pp. 71-77, XP 004381373.
Hemmi et al., "A Toll-like receptor recognizes bacterial DNA," Nature, MacMillan Journals Ltd., London, GB, vol. 408, No. 6813, Dec. 7, 2000, pp. 740-745, XP 002168474.
Application and File History for U.S. Appl. No. 10/528,235, filed Jul. 30, 2008, inventor Schmidt et al.

* cited by examiner

*Primary Examiner* — Prabha Chunduru
(74) *Attorney, Agent, or Firm* — Douglas J. Christensen

(57) ABSTRACT

The invention relates to a method for separating and/or enriching prokaryotic DNA, comprising the following steps: a) contacting of at least one prokaryotic DNA that is in solution with a protein that bonds specifically to prokaryotic DNA, the protein being 25%-35% homologous with the wild-type CGPB protein, thus forming a protein-DNA complex; and b) separation of the complex. The invention also relates to a kit for carrying out said method.

26 Claims, 13 Drawing Sheets

```
                          10         20         30         40         50
CPGbP656    1 MEGDGSDPEP PDAGEDSKSE NGENAPIYCI CRKPDINCFM IGCDNCNEWF
CPGbP241    1 ---------- ---------- ---------- ---------- ----------
CPGbP181    1 ---------- ---------- ---------- ---------- ----------

60         70         80         90        100
CPGbP656   51 HGDCIRITEK MAKAIREWYC RECREKDPKL EIRYRHKKSR ERDGNERDSS
CPGbP241   51 ---------- ---------- ---------- ---------- ----------
CPGbP181   51 ---------- ---------- ---------- ---------- ----------

110        120        130        140        150
CPGbP656  101 EPRDEGGGRK RPVPDPNLQR RAGSGTGVGA MLARGSASPH KSSPQPLVAT
CPGbP241  101 -----GGGRK RPVPDPNLQR RAGSGTGVGA MLARGSASPH KSSPQPLVAT
CPGbP181  101 -----GGGRK RPVPDPNLQR RAGSGTGVGA MLARGSASPH KSSPQPLVAT 160        170        180        190        200
CPGbP656  151 PSQHHQQQQQ QIKRSARMCG ECEACRRTED CGHCDFCRDM KKFGGPNKIR
CPGbP241  151 PSQHHQQQQQ QIKRSARMCG ECEACRRTED CGHCDFCRDM KKFGGPNKIR
CPGbP181  151 PSQHHQQQQQ QIKRSARMCG ECEACRRTED CGHCDFCRDM KKFGGPNKIR 210        220        230        240        250
CPGbP656  201 QKCRLRQCQL RARESYKYFP SSLSPVTPSE SLPRPRRPLP TQQQPQPSQK
CPGbP241  201 QKCRLRQCQL RARESYKYFP SSLSPVTPSE SLPRPRRPLP TQQQPQPSQK
CPGbP181  201 QKCRLRQCQL RARESYKYFP SSLSPVTPSE SLPRPRRPLP TQQQPQPSQK 260        270        280        290        300
CPGbP656  251 LGRIREDEGA VASSTVKEPP EATATPEPLS DEDLPLDPDL YQDFCAGAFD
CPGbP241  251 LGRIREDEGA VASSTVKEPP EATATPEPLS DEDLPLDPDL YQDFCAGAFD
CPGbP181  251 LGRIREDEGA VASSTVKEPP EATATPEPLS DEDLPL---- ----------

310        320        330        340        350
CPGbP656  301 DNGLPWMSDT EESPFLDPAL RKRAVKVKHV KRREKKSEKK KEERYKRHRQ
CPGbP241  301 DNGLPWMSDT EESPFLDPAL RKRAVKVKHV KRREKKSEKK KEERYK----

360        370        380        390        400
CPGbP656  351 KQKHKDKWKH PERADAKDPA SLPQCLGPGC VRPAQPSSKY CSDDCGMKLA 410        420        430        440        450
CPGbP656  401 ANRIYEILPQ RIQQWQQSPC IAEEHGKKLL ERIRREQQSA RTRLQEMERR 460        470        480        490        500
CPGbP656  451 FHELEAIILR AKQQAVREDE ESNEGDSDDT DLQIFCVSCG HPINPRVALR 510        520        530        540        550
CPGbP656  501 HMERCYAKYE SQTSFGSMYP TRIEGATRLF CDVYNPQSKT YCKRLQVLCP 560        570        580        590        600
CPGbP656  551 EHSRDPKVPA DEVCGCPLVR DVFELTGDFC RLPKRQCNRH YCWEKLRRAE 610        620        630        640        650
CPGbP656  601 VDLERVRVWY KLDELFEQER NVRTAMTNRA GLLALMLHQT IQHDPLTTDL 660        670        680        690        700
CPGbP656  651 RSSADR.... .......... .......... .......... ..........
```

```
                    9              18              27              36              45              54
5' ATG GAG GGA GAT GGT TCA GAC CCA GAG CCT CCA GAT GCC GGG GAG GAC AGC AAG
   --- --- --- --- --- --- --- --- --- --- --- --- --- --- --- --- --- ---
    M   E   G   D   G   S   D   P   E   P   P   D   A   G   E   D   S   K 63              72              81              90              99             108
   TCC GAG AAT GGG GAG AAT GCG CCC ATC TAC TGC ATC TGC CGC AAA CCG GAC ATC
   --- --- --- --- --- --- --- --- --- --- --- --- --- --- --- --- --- ---
    S   E   N   G   E   N   A   P   I   Y   C   I   C   R   K   P   D   I 117             126             135             144             153             162
   AAC TGC TTC ATG ATC GGG TGT GAC AAC TGC AAT GAG TGG TTC CAT GGG GAC TGC
   --- --- --- --- --- --- --- --- --- --- --- --- --- --- --- --- --- ---
    N   C   F   M   I   G   C   D   N   C   N   E   W   F   H   G   D   C 171             180             189             198             207             216
   ATC CGG ATC ACT GAG AAG ATG GCC AAG GCC ATC CGG GAG TGG TAC TGT CGG GAG
   --- --- --- --- --- --- --- --- --- --- --- --- --- --- --- --- --- ---
    I   R   I   T   E   K   M   A   K   A   I   R   E   W   Y   C   R   E 225             234             243             252             261             270
   TGC AGA GAG AAA GAC CCC AAG CTA GAG ATT CGC TAT CGG CAC AAG AAG TCA CGG
   --- --- --- --- --- --- --- --- --- --- --- --- --- --- --- --- --- ---
    C   R   E   K   D   P   K   L   E   I   R   Y   R   H   K   K   S   R 279             288             297             306             315             324
   GAG CGG GAT GGC AAT GAG CGG GAC AGC AGT GAG CCC CGG GAT GAG GGT GGA GGG
   --- --- --- --- --- --- --- --- --- --- --- --- --- --- --- --- --- ---
    E   R   D   G   N   E   R   D   S   S   E   P   R   D   E   G   G   G
                                                                    G   G   G 333             342             351             360             369             378
   CGC AAG AGG CCT GTC CCT GAT CCA AAC CTG CAG CGC CGG GCA GGG TCA GGG ACA
   --- --- --- --- --- --- --- --- --- --- --- --- --- --- --- --- --- ---
    R   K   R   P   V   P   D   P   N   L   Q   R   R   A   G   S   G   T
    R   K   R   P   V   P   D   P   N   L   Q   R   R   A   G   S   G   T 387             396             405             414             423             432
   GGG GTT GGG GCC ATG CTT GCT CGG GGC TCT GCT TCG CCC CAC AAA TCC TCT CCG
   --- --- --- --- --- --- --- --- --- --- --- --- --- --- --- --- --- ---
    G   V   G   A   M   L   A   R   G   S   A   S   P   H   K   S   S   P
    G   V   G   A   M   L   A   R   G   S   A   S   P   H   K   S   S   P 441             450             459             468             477             486
   CAG CCC TTG GTG GCC ACA CCC AGC CAG CAT CAC CAG CAG CAG CAG CAG CAG ATC
   --- --- --- --- --- --- --- --- --- --- --- --- --- --- --- --- --- ---
    Q   P   L   V   A   T   P   S   Q   H   H   Q   Q   Q   Q   Q   Q   I
    Q   P   L   V   A   T   P   S   Q   H   H   Q   Q   Q   Q   Q   Q   I 495             504             513             522             531             540
   AAA CGG TCA GCC CGC ATG TGT GGT GAG TGT GAG GCA TGT CGG CGC ACT GAG GAC
   --- --- --- --- --- --- --- --- --- --- --- --- --- --- --- --- --- ---
    K   R   S   A   R   M   C   G   E   C   E   A   C   R   R   T   E   D
    K   R   S   A   R   M   C   G   E   C   E   A   C   R   R   T   E   D
```

Fig. 2 (Continued)

```
            549             558             567             576             585             594
TGT GGT CAC TGT GAT TTC TGT CGG GAC ATG AAG AAG TTC GGG GGC CCC AAC AAG
--- --- --- --- --- --- --- --- --- --- --- --- --- --- --- --- --- ---
 C   G   H   C   D   F   C   R   D   M   K   K   F   G   G   P   N   K
 C   G   H   C   D   F   C   R   D   M   K   K   F   G   G   P   N   K 603             612             621             630             639             648
ATC CGG CAG AAG TGC CGG CTG CGC CAG TGC CAG CTG CGG GCC CGG GAA TCG TAC
--- --- --- --- --- --- --- --- --- --- --- --- --- --- --- --- --- ---
 I   R   Q   K   C   R   L   R   Q   C   Q   L   R   A   R   E   S   Y
 I   R   Q   K   C   R   L   R   Q   C   Q   L   R   A   R   E   S   Y 657             666             675             684             693             702
AAG TAC TTC CCT TCC TCG CTC TCA CCA GTG ACG CCC TCA GAG TCC CTG CCA AGG
--- --- --- --- --- --- --- --- --- --- --- --- --- --- --- --- --- ---
 K   Y   F   P   S   S   L   S   P   V   T   P   S   E   S   L   P   R
 K   Y   F   P   S   S   L   S   P   V   T   P   S   E   S   L   P   R 711             720             729             738             747             756
CCC CGC CGG CCA CTG CCC ACC CAA CAG CAG CCA CAG CCA TCA CAG AAG TTA GGG
--- --- --- --- --- --- --- --- --- --- --- --- --- --- --- --- --- ---
 P   R   R   P   L   P   T   Q   Q   Q   P   Q   P   S   Q   K   L   G
 P   R   R   P   L   P   T   Q   Q   Q   P   Q   P   S   Q   K   L   G 765             774             783             792             801             810
CGC ATC CGT GAA GAT GAG GGG GCA GTG GCG TCA TCA ACA GTC AAG GAG CCT CCT
--- --- --- --- --- --- --- --- --- --- --- --- --- --- --- --- --- ---
 R   I   R   E   D   E   G   A   V   A   S   S   T   V   K   E   P   P
 R   I   R   E   D   E   G   A   V   A   S   S   T   V   K   E   P   P
            819             828             837             846             855             864
GAG GCT ACA GCC ACA CCT GAG CCA CTC TCA GAT GAG GAC CTA CCT CTG GAT CCT
--- --- --- --- --- --- --- --- --- --- --- --- --- --- --- --- --- ---
 E   A   T   A   T   P   E   P   L   S   D   E   D   L   P   L   D   P
 E   A   T   A   T   P   E   P   L   S   D   E   D   L   P   L
            873             882             891             900             909             918
GAC CTG TAT CAG GAC TTC TGT GCA GGG GCC TTT GAT GAC AAT GGC CTG CCC TGG
--- --- --- --- --- --- --- --- --- --- --- --- --- --- --- --- --- ---
 D   L   Y   Q   D   F   C   A   G   A   F   D   D   N   G   L   P   W 927             936             945             954             963             972
ATG AGC GAC ACA GAA GAG TCC CCA TTC CTG GAC CCC GCG CTG CGG AAG AGG GCA
--- --- --- --- --- --- --- --- --- --- --- --- --- --- --- --- --- ---
 M   S   D   T   E   E   S   P   F   L   D   P   A   L   R   K   R   A 981             990             999            1008            1017            1026
GTG AAA GTG AAG CAT GTG AAG CGT CGG GAG AAG AAG TCT GAG AAG AAG AAG GAG
--- --- --- --- --- --- --- --- --- --- --- --- --- --- --- --- --- ---
 V   K   V   K   H   V   K   R   R   E   K   K   S   E   K   K   K   E 1035            1044            1053            1062            1071            1080
GAG CGA TAC AAG CGG CAT CGG CAG AAG CAG AAG CAC AAG GAT AAA TGG AAA CAC
--- --- --- --- --- --- --- --- --- --- --- --- --- --- --- --- --- ---
 E   R   Y   K   R   H   R   Q   K   Q   K   H   K   D   K   W   K   H 1089            1098            1107            1116            1125            1134
CCA GAG AGG GCT GAT GCC AAG GAC CCT GCG TCA CTG CCC CAG TGC CTG GGG CCC
--- --- --- --- --- --- --- --- --- --- --- --- --- --- --- --- --- ---
 P   E   R   A   D   A   K   D   P   A   S   L   P   Q   C   L   G   P
```

Fig. 2 (Continued)

```
        1143            1152            1161            1170            1179            1188
GGC TGT GTG CGC CCC GCC CAG CCC AGC TCC AAG TAT TGC TCA GAT GAC TGT GGC
--- --- --- --- --- --- --- --- --- --- --- --- --- --- --- --- --- ---
 G   C   V   R   P   A   Q   P   S   S   K   Y   C   S   D   D   C   G 1197            1206            1215            1224            1233            1242
ATG AAG CTG GCA GCC AAC CGC ATC TAC GAG ATC CTC CCC CAG CGC ATC CAG CAG
--- --- --- --- --- --- --- --- --- --- --- --- --- --- --- --- --- ---
 M   K   L   A   A   N   R   I   Y   E   I   L   P   Q   R   I   Q   Q 1251            1260            1269            1278            1287            1296
TGG CAG CAG AGC CCT TGC ATT GCT GAA GAG CAC GGC AAG AAG CTG CTC GAA CGC
--- --- --- --- --- --- --- --- --- --- --- --- --- --- --- --- --- ---
 W   Q   Q   S   P   C   I   A   E   E   H   G   K   K   L   L   E   R 1305            1314            1323            1332            1341            1350
ATT CGC CGA GAG CAG CAG AGT GCC CGC ACC CGC CTT CAG GAA ATG GAA CGC CGA
--- --- --- --- --- --- --- --- --- --- --- --- --- --- --- --- --- ---
 I   R   R   E   Q   Q   S   A   R   T   R   L   Q   E   M   E   R   R 1359            1368            1377            1386            1395            1404
TTC CAT GAG CTT GAG GCC ATC ATT CTA CGT GCC AAG CAG CAG GCT GTG CGC GAG
--- --- --- --- --- --- --- --- --- --- --- --- --- --- --- --- --- ---
 F   H   E   L   E   A   I   I   L   R   A   K   Q   Q   A   V   R   E 1413            1422            1431            1440            1449            1458
GAT GAG GAG AGC AAC GAG GGT GAC AGT GAT GAC ACA GAC CTG CAG ATC TTC TGT
--- --- --- --- --- --- --- --- --- --- --- --- --- --- --- --- --- ---
 D   E   E   S   N   E   G   D   S   D   D   T   D   L   Q   I   F   C 1467            1476            1485            1494            1503            1512
GTT TCC TGT GGG CAC CCC ATC AAC CCA CGT GTT GCC TTG CGC CAC ATG GAG CGC
--- --- --- --- --- --- --- --- --- --- --- --- --- --- --- --- --- ---
 V   S   C   G   H   P   I   N   P   R   V   A   L   R   H   M   E   R 1521            1530            1539            1548            1557            1566
TGC TAC GCC AAG TAT GAG AGC CAG ACG TCC TTT GGG TCC ATG TAC CCC ACA CGC
--- --- --- --- --- --- --- --- --- --- --- --- --- --- --- --- --- ---
 C   Y   A   K   Y   E   S   Q   T   S   F   G   S   M   Y   P   T   R 1575            1584            1593            1602            1611            1620
ATT GAA GGG GCC ACA CGA CTC TTC TGT GAT GTG TAT AAT CCT CAG AGC AAA ACA
--- --- --- --- --- --- --- --- --- --- --- --- --- --- --- --- --- ---
 I   E   G   A   T   R   L   F   C   D   V   Y   N   P   Q   S   K   T 1629            1638            1647            1656            1665            1674
TAC TGT AAG CGG CTC CAG GTG CTG TGC CCC GAG CAC TCA CGG GAC CCC AAA GTG
--- --- --- --- --- --- --- --- --- --- --- --- --- --- --- --- --- ---
 Y   C   K   R   L   Q   V   L   C   P   E   H   S   R   D   P   K   V 1683            1692            1701            1710            1719            1728
CCA GCT GAC GAG GTA TGC GGG TGC CCC CTT GTA CGT GAT GTC TTT GAG CTC ACG
--- --- --- --- --- --- --- --- --- --- --- --- --- --- --- --- --- ---
 P   A   D   E   V   C   G   C   P   L   V   R   D   V   F   E   L   T 1737            1746            1755            1764            1773            1782
GGT GAC TTC TGC CGC CTG CCC AAG CGC CAG TGC AAT CGC CAT TAC TGC TGG GAG
--- --- --- --- --- --- --- --- --- --- --- --- --- --- --- --- --- ---
 G   D   F   C   R   L   P   K   R   Q   C   N   R   H   Y   C   W   E
```

Fig. 2 (Continued)

```
         1791            1800            1809            1818            1827            1836
    AAG CTG CGG CGT GCG GAA GTG GAC TTG GAG CGC GTG CGT GTG TGG TAC AAG CTG
    --- --- --- --- --- --- --- --- --- --- --- --- --- --- --- --- --- ---
     K   L   R   R   A   E   V   D   L   E   R   V   R   V   W   Y   K   L 1845            1854            1863            1872            1881            1890
    GAC GAG CTG TTT GAG CAG GAG CGC AAT GTG CGC ACA GCC ATG ACA AAC CGC GCG
    --- --- --- --- --- --- --- --- --- --- --- --- --- --- --- --- --- ---
     D   E   L   F   E   Q   E   R   N   V   R   T   A   M   T   N   R   A 1899            1908            1917            1926            1935            1944
    GGA TTG CTG GCC CTG ATG CTG CAC CAG ACG ATC CAG CAC GAT CCC CTC ACT ACC
    --- --- --- --- --- --- --- --- --- --- --- --- --- --- --- --- --- ---
     G   L   L   A   L   M   L   H   Q   T   I   Q   H   D   P   L   T   T 1953            1962            1971
    GAC CTG CGC TCC AGT GCC GAC CGC TGA 3'
    --- --- --- --- --- --- --- --- ---
     D   L   R   S   S   A   D   R   *
```

Results of PCR after enrichment of prokaryotic DNA
from a DNA mixture of *Staphylococcus aureus* and human DNA
using coupled CpGbP-181 protein on CNBr sepharose Legend:

1 $E_1$ (E= elution fraction)   6 prior to column
2 $E_2$                          7 pos. control
3 $E_3$                          8 pGEM marker
4 $E_4$
5 $E_5$ Results of PCR after enrichment of prokaryotic DNA from a DNA mixture of *Staphylococcus aureus* and human DNA using coupled CpG-181 protein on AH sepharose Legend:

1  $E_1$ (E= elution fraction)
2  $E_2$
3  $E_3$
4  $E_4$
5  $E_5$
6  negative control
7  prior to column
8  positive control
9  BIORAD marker

SEQUENCE LISTING

<160> NUMBER OF SEQ ID NOS: 8

<210> SEQ ID NO 1
<211> LENGTH: 543
<212> TYPE: DNA
<213> ORGANISM: Homo sapiens
<220> FEATURE:
<221> NAME/KEY: CDS
<222> LOCATION: (1)..(543)

<400> SEQUENCE: 1

```
ggt gga ggg cgc aag agg cct gtc cct gat cca aac ctg cag cgc cgg      48
Gly Gly Gly Arg Lys Arg Pro Val Pro Asp Pro Asn Leu Gln Arg Arg
1               5                   10                  15 gca ggg tca ggg aca ggg gtt ggg gcc atg ctt gct cgg ggc tct gct      96
Ala Gly Ser Gly Thr Gly Val Gly Ala Met Leu Ala Arg Gly Ser Ala
            20                  25                  30 tcg ccc cac aaa tcc tct ccg cag ccc ttg gtg gcc aca ccc agc cag     144
Ser Pro His Lys Ser Ser Pro Gln Pro Leu Val Ala Thr Pro Ser Gln
        35                  40                  45 cat cac cag cag cag cag cag cag atc aaa cgg tca gcc cgc atg tgt     192
His His Gln Gln Gln Gln Gln Gln Ile Lys Arg Ser Ala Arg Met Cys
    50                  55                  60 ggt gag tgt gag gca tgt cgg cgc act gag gac tgt ggt cac tgt gat     240
Gly Glu Cys Glu Ala Cys Arg Arg Thr Glu Asp Cys Gly His Cys Asp
65                  70                  75                  80 ttc tgt cgg gac atg aag aag ttc ggg ggc ccc aac aag atc cgg cag     288
Phe Cys Arg Asp Met Lys Lys Phe Gly Gly Pro Asn Lys Ile Arg Gln
                85                  90                  95 aag tgc cgg ctg cgc cag tgc cag ctg cgg gcc cgg gaa tcg tac aag     336
```

```
Lys Cys Arg Leu Arg Gln Cys Gln Leu Arg Ala Arg Glu Ser Tyr Lys
            100                 105                 110 tac ttc cct tcc tcg ctc tca cca gtg acg ccc tca gag tcc ctg cca      384
Tyr Phe Pro Ser Ser Leu Ser Pro Val Thr Pro Ser Glu Ser Leu Pro
            115                 120                 125 agg ccc cgc cgg cca ctg ccc acc caa cag cag cca cag cca tca cag      432
Arg Pro Arg Arg Pro Leu Pro Thr Gln Gln Gln Pro Gln Pro Ser Gln
            130                 135                 140 aag tta ggg cgc atc cgt gaa gat gag ggg gca gtg gcg tca tca aca      480
Lys Leu Gly Arg Ile Arg Glu Asp Glu Gly Ala Val Ala Ser Ser Thr
145                 150                 155                 160 gtc aag gag cct cct gag gct aca gcc aca cct gag cca ctc tca gat      528
Val Lys Glu Pro Pro Glu Ala Thr Ala Thr Pro Glu Pro Leu Ser Asp
                165                 170                 175 gag gac cta cct ctg                                                  543
Glu Asp Leu Pro Leu
            180

<210> SEQ ID NO 2
<211> LENGTH: 181
<212> TYPE: PRT
<213> ORGANISM: Homo sapiens

<400> SEQUENCE: 2

Gly Gly Gly Arg Lys Arg Pro Val Pro Asp Pro Asn Leu Gln Arg Arg
1               5                   10                  15

Ala Gly Ser Gly Thr Gly Val Gly Ala Met Leu Ala Arg Gly Ser Ala
            20                  25                  30

Ser Pro His Lys Ser Ser Pro Gln Pro Leu Val Ala Thr Pro Ser Gln
        35                  40                  45

His His Gln Gln Gln Gln Gln Ile Lys Arg Ser Ala Arg Met Cys
    50                  55                  60

Gly Glu Cys Glu Ala Cys Arg Arg Thr Glu Asp Cys Gly His Cys Asp
65                  70                  75                  80

Phe Cys Arg Asp Met Lys Lys Phe Gly Gly Pro Asn Lys Ile Arg Gln
                85                  90                  95

Lys Cys Arg Leu Arg Gln Cys Gln Leu Arg Ala Arg Glu Ser Tyr Lys
            100                 105                 110

Tyr Phe Pro Ser Ser Leu Ser Pro Val Thr Pro Ser Glu Ser Leu Pro
            115                 120                 125

Arg Pro Arg Arg Pro Leu Pro Thr Gln Gln Gln Pro Gln Pro Ser Gln
            130                 135                 140

Lys Leu Gly Arg Ile Arg Glu Asp Glu Gly Ala Val Ala Ser Ser Thr
145                 150                 155                 160

Val Lys Glu Pro Pro Glu Ala Thr Ala Thr Pro Glu Pro Leu Ser Asp
                165                 170                 175

Glu Asp Leu Pro Leu
            180

<210> SEQ ID NO 3
<211> LENGTH: 28
<212> TYPE: DNA
<213> ORGANISM: Artificial sequence
<220> FEATURE:
<223> OTHER INFORMATION: Description of artificial sequence: Primer

<400> SEQUENCE: 3
ggatccggtg gagggcgcaa gaggcctg                                        28
```

```
<210> SEQ ID NO 4
<211> LENGTH: 27
<212> TYPE: DNA
<213> ORGANISM: Artificial sequence
<220> FEATURE:
<223> OTHER INFORMATION: Description of artificial sequence: Primer

<400> SEQUENCE: 4
aagcttagag gtaggtcctc atctgag                                               27

<210> SEQ ID NO 5
<211> LENGTH: 26
<212> TYPE: DNA
<213> ORGANISM: Artificial sequence
<220> FEATURE:
<223> OTHER INFORMATION: Description of artificial sequence: Primer

<400> SEQUENCE: 5
agcatacaag caaatttttt acaccg                                                26

<210> SEQ ID NO 6
<211> LENGTH: 24
<212> TYPE: DNA
<213> ORGANISM: Artificial sequence
<220> FEATURE:
<223> OTHER INFORMATION: Description of artificial sequence: Primer

<400> SEQUENCE: 6
gttctgttat tgacacccgc aatt                                                  24

<210> SEQ ID NO 7
<211> LENGTH: 24
<212> TYPE: DNA
<213> ORGANISM: Artificial sequence
<220> FEATURE:
<223> OTHER INFORMATION: Description of artificial sequence: Primer

<400> SEQUENCE: 7
ccttcctaat aatcctgcgg atgt                                                  24

<210> SEQ ID NO 8
<211> LENGTH: 28
<212> TYPE: DNA
<213> ORGANISM: Artificial sequence
<220> FEATURE:
<223> OTHER INFORMATION: Description of artificial sequence: Primer

<400> SEQUENCE: 8
ctgaaggtag cattagtctt tgataacg                                              28
```

METHOD FOR ENRICHING AND/OR SEPARATING PROKARYOTIC DNA USING A PROTEIN THAT SPECIFICALLY BONDS TO UNMETHYLATED DNA CONTAINING CPG-MOTIFS

BACKGROUND OF THE INVENTION

1. Field of the Invention

The invention relates to a method of separating and/or enriching prokaryotic DNA or of depleting said DNA from physiological liquids using a protein which specifically binds non-methylated cytidine-phosphate-guanosine dinucleotides (CpG motifs) of DNA, as well as to a kit for carrying out said method.

2. Background

Infections caused by bacteria are one of the most frequent causes of inflammatory diseases. For the prognosis of the clinical cause as well as, in particular, for timely selection of suitable therapeutic measures, early detection of the bacterial pathogens is of decisive importance.

In the detection of bacterial pathogens use is made even today, above all, of different methods of cultivating cells. However, current studies clearly show the poor suitability of culture-dependent methods for detection of pathogens (Hellebrand W., König-Bruhns C., Hass W., Studie zur Blutkulturdiagnostik im Jahr 2002, Poster Jahrestagung der Deutschen Gesellschaft Für Hygiene und Mikrobiologie, Göttingen 2004; Straube E (2003) Sepsis—microbiological diagnosis. Infection 31:284). According to these studies, it was possible to determine pathogens in only approximately 15-16% of all blood cultures examined. As a result of the disadvantages of these methods, increased efforts were made to find alternatives, especially during the past decade, simultaneously with the rapid technological development in molecular biology. First reports on the use of culture-independent methods of detecting bacterial pathogens, based on the principal of the polymerase chain reaction (PCR), date back to the early 1990s. Thus, for instance, Miller and colleagues (Miller N J Clin Microbiol. 1994 (February;32(2):393-7) were able to show that culture-independent methods are superior to the classic techniques of cultivation and microscopy for detection of *mycobacterium tuberculosis*. However, further molecular-biological methods based on the detection of pathogen-specific nucleic acids have gained importance (e.g. M. Grijalva et al. Heart 89 (2003) 263-268; Uyttendaele M et al. Lett Appl Microbiol. 2003;37(5):386-91; Saukkoriipi A et al. Mol Diagn. March 2003;7(1):9-15; Tzanakaki G et al. FEMS Immunol Med Microbiol. Oct. 24, 2003;39(1):31-6). In addition to the high specificity of such molecular-biological methods, the reduced time expenditure is to be mentioned as a substantial advantage over conventional culture-dependent methods. However, the sensitivity of the detection of prokaryotic DNA directly from body fluids and not from pre-treated testing material as compared to the culture of microorganisms has been much too low so far. An amount of nucleic acids of bacteria sufficient for the directed detection of pathogens from testing material, which is not pre-treated, is achieved to a limited extent only also with respect to the 16S-rRNA analysis, by means of PCR of the 16S region on the bacterial chromosome and the subsequent sequence analysis of the PCR fragment, because in most cases, several copies of the segment encoding 16S-rRNA are found on the chromosome. The direct specific detection of pathogens by means of 16S-rRNA analysis requires that only one species of pathogen is present in the sample to be examined. If there are different species of pathogens in the sample, specific detection by sequencing of the 16S-rRNA region is not possible, because the primers used are universal for most bacteria. Further, it is a prerequisite to the detection of pathogens by 16S-rRNA analysis that the bacteria to be detected are present in the metabolic phase and sufficiently express 16S-rRNA. This is usually not the case, in particular in patients subject to calculated antibiotic therapy. Moreover, expression of certain pathogenicity factors of bacteria does not occur at all times, although the corresponding genes are present in the bacterial genome. As a result, erroneously negative results are transmitted to the clinical physician. Thus, selective antibiotic therapy may be initiated either not at all or much too late. In such cases, the physician has to rely on his knowledge gained by experience and on general guidelines (such as those of the Paul Ehrlich Foundation) and will therefore effect a much too general antibiotic treatment. The unspecific use of antibiotics bears a number of risks, not only for the individual patient (such as unnecessary side effects in the form of renal damage etc.), but also for the entire society (e.g. the development of additional antibiotic resistances, such as MRSA (methicilline-resistant *Staphylococcus aureus*, etc.). Therefore, the detection of clinically meaningful pathogenicity factors and resistances of bacteria at the chromosomal level and at the plasmid level, i.e. ultimately on the DNA level, provides considerable advantages for the diagnosis of many infectious diseases but also of sepsis. This applies even more because, at this level, a distinction can also be made between pathogenic and commensal bacteria.

Most frequently, the detection of pathogen-specific nucleic acids is effected by nucleic acid amplification techniques (NAT), such as the amplification of the prokaryotic DNA by means of the polymerase chain reaction (PCR) or the ligase chain reaction (LCR), respectively. The high specificity and fast availability of the results is contrasted by the susceptibility to interference by contamination or by strongly reaction-inhibiting factors of clinical samples.

In a conventional PCR detection method, successful detection of pathogens in the blood theoretically requires at least 1 target DNA of the pathogen to be present in 10 µl of blood. This corresponds to approximately 100 targets in 1 ml of blood or 1,000 targets in 10 ml of blood, respectively. Things are different with regard to the blood culture for detection of infection pathogens. In this case, the lower detection limit is approximately 3-5 bacteria per 10 ml of blood.

This detection limit is presently not reached yet by PCR methods, not even by those which have their target sequences in the vicinity of the 16S-rRNA region on the chromosome. Although several regions encoding 16S-rRNA are located on the bacterial chromosome, in most cases 3 to 6, the prerequisite that at least one molecule of the template DNA is located in the PCR reaction mixture is not met.

Improved diagnostic safety is to be expected of PCR methods whose specific target sequences encode species-specific proteins, either in the chromosome or on plasmids of the microorganisms. The above remarks with respect to the detection limit also apply here. Especially under the action of a current antibiotic therapy, growth of the pathogens can be considerably decelerated, limited or blocked, even if the antibiotic employed ultimately does not have an optimal effect. This situation is often found especially in patients who are already receiving antibiotic treatment and in whom, therefore, no disease-causing bacteria can be grown from blood cultures or other samples (such as for example tracheal smears, broncho-alveolar lavages (BAL) etc.).

Due to insufficient sensitivity, the detection of pathogen-specific nucleic acids without an amplification step by direct detection of prokaryotic DNA (probe technique, FISH technique) is of diagnostic importance only at a sufficiently high germ count in the test material.

The essential problems of the detection of prokaryotic DNA for identification of bacterial pathogens in body fluids consist, in addition to PCR-inhibiting ingredients in the test material, mainly in the low concentration of prokaryotic DNA and the resulting excess of eukaryotic DNA versus prokaryotic DNA. In this connection, in particular, competitive processes in DNA analysis as well as the quantity of prokaryotic DNA can be regarded as a hindrance to qualitative and quantitative detection of pathogens.

The usual methods of DNA isolation enrich the total DNA of a body fluid so that the ratio of host DNA to microbial DNA may be between $1:10^{-6}$ and $1:10^{-8}$. This difference makes the difficulty in detecting microbial DNA in body fluids quite easy to understand.

Prokaryotic DNA differs from eukaryotic DNA, for example, by the presence of non-methylated CpG motifs (Hartmann G et al., Deutsches Ärzteblatt, Jg. 98/15:A981-A985 (2001). In the prokaryotic DNA, 16 times more CpG motifs are present than in eukaryotic DNA, which contains such motifs only temporarily, for example in cancer cells or promoter regions. These motifs are not methylated in prokaryotic DNA, whereas the majority of them are methylated in eukaryotic DNA, which further augments their distinctiveness. Non-methylated CpG motifs are non-methylated desoxycytidylate-desoxyguanylate-dinucleotides within the prokaryotic genome or within fragments thereof.

It is further known that diagnostic statements for cancers can be derived from different methylation patterns within the human DNA (Epigenetics in Cancer Prevention: Early Detection and Risk Assessment (Annals of the New York Academy of Sciences, Vol 983) Editor: Mukesh Verma ISBN 1-57331-431-5). Methylated and non-methylated cytosines in the genome allow tissue-specific but also disease-specific patterns to be identified. The specific methylation patterns of a disease allow, on the one hand, diagnosis at a very early point in time and, on the other hand, molecular classification of a disease and the likely response of a patient to a certain treatment. For detailed information on this, see, for example, Beck S, Olek A, Walter J.: From genomics to epigenomics: a loftier view of life.", Nature Biotechnology 1999 Dec;17(12):1144, on the homepage of Epigenomics AG , or WO 200467775.

Cross at el. showed that it is possible to separate differently methylated genomic human DNA by binding the methylated CpG motifs to a protein (Cross S H, Chariton J A, Nan X, Bird A P, Purification of CpG islands using a methylated DNA binding column, Nat Genet. March 1994;6(3):236-44). Thus, this method serves to bind DNA containing methylated CpG motifs. Sufficient isolation of non-methylated and methylated DNA is not possible for technical reasons, because the protein used also weakly binds non-methylated DNA. It is also not possible with these methods to enrich non-methylated DNA, because the capacity of the protein used is not sufficient to separate non-methylated DNA to a sufficient extent in the case of a high excess of methylated DNA. Further, due to the binding of the methylated DNA, the initial volume in which the non-methylated DNA is present, remains unchanged so that no enrichment is achieved.

Thus it would be desirable to separate non-methylated DNA from methylated DNA and to be able to enrich non-methylated DNA so as to separate prokaryotic DNA from eukaryotic DNA or differently methylated human DNA, respectively, from each other. In addition, it would be desirable and of great interest in terms of health economics if the isolation and enrichment of non-methylated DNA could also be obtained from a mixture (for example, full blood) which is characterized by a great excess of methylated DNA.

It is known from Voo et al. that human CpG-binding protein (hCGBP) is capable of binding non-methylated CpG motifs. This publication describes the transcription-activating factor hCGBP which has been shown to play a role in the regulation of gene expression in CpG motifs.

EP 02020904 shows a method which enables isolation and enrichemnt of prokaryotic DNA from a mixture of prokaryotic and eukaryotic DNA by binding the prokaryotic DNA to a protein which specifically binds non-methylated DNA.

SUMMARY

Therefore, it is an object of the present invention to provide a method of separating and/or enriching prokaryotic DNA from examination samples having a high content of eukaryotic DNA, in particular from patients with infections.

According to the invention, this is achieved by a protein binding non-methylated CpG motifs, said protein having a 25% to 35% homology, in particular approximately 27.6% homology, with wild type CGBP protein and is shortened with respect to the latter, to the length of the binding site at maximum.

The human CGBP protein (cf. Voo et al., Mol Cell Biol. 200 Mar; 20(6):2 2108-21) is referred to hereinafter as wild type CGBP protein (or CPGbP656). The protein according to the invention is referred to hereinafter as CPGbP181. The protein described in EP 02020904, which is a shortened variant of the wild type CGBP protein and served as the basis for the protein according to the invention, is referred to hereinafter as CPGbP241.

BRIEF DESCRIPTION OF THE FIGURES

The invention will be described below with respect to the Figures, wherein:

FIG. 1 shows the amino acid sequence of CPGbP 181 (in bold print) compared with the wild type CGBP protein (CPGbP656) and CPGbP241 (printed in italics);

FIG. 2 shows the DNA sequence and translation to the amino acid sequence of the complete CPG-binding protein CPGbP656, wherein the shortened CPG-binding peptides CPGbP241 (bold) and CPGbP181 (SEQ. ID No:1, italics) are shown;

DETAILED DESCRIPTION

Figure 3:
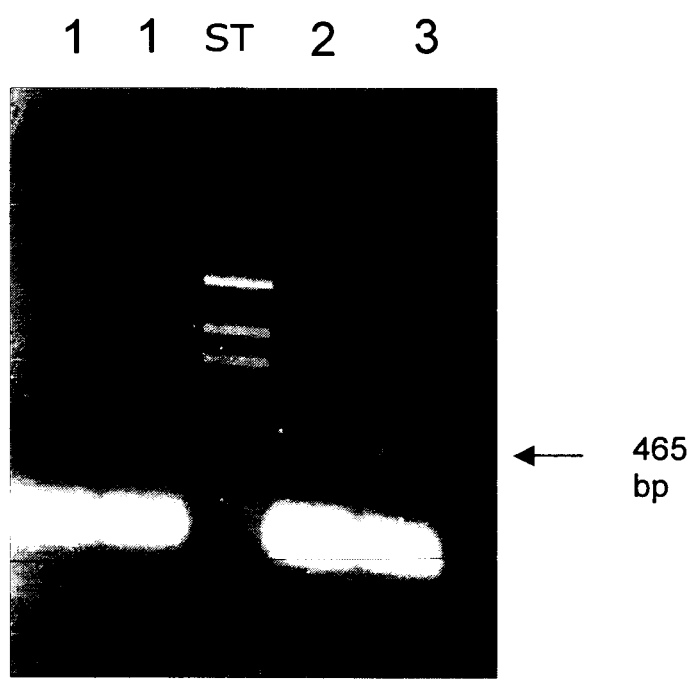
FIG. 3 shows a PCR of streptococci-DNA in human blood.

The wild type CGBP protein CPGbP656 binds non-methylated CpG motifs of prokaryotic DNA, thus forming a protein-DNA complex. This complex may be or become attached to, for example, a carrier, whereby separation and/or enrichment of DNA can be effected. The present invention is now based on the surprising finding that a protein which is shortened relative to the wild type CGBP protein (CPGbP656 comprising 656 amino acids) and presenting 25% to 35%, in particular approximately 27.6%, homology with the wild type CGBP protein, has improved binding properties over non-methylated CpG motifs of prokaryotic DNA than the wild type CGBP protein and variants thereof with a homology of 80% or more. An example of such shortened protein is CPGbP181 with 181 amino acids.

Prokaryotic DNA differs from eukaryotic DNA, for example, by the presence of non-methylated CpG motifs (Deutsches Ärzteblatt, Jg. 98/15: A981-A985 (2001)). The invention is based on the finding that eukaryotic DNA and prokaryotic DNA differ in their proportion of CpG motifs. In prokaryotic DNA, CpG motifs are present with a 20-fold excess as compared to eukaryotic DNA, which contains such motifs only temporarily, e.g. in cancer cells or promoter regions (Deutsches Ärzteblatt, Jg. 98/15: A981-A985 (2001)). In prokaryotic DNA, these motifs are not methylated, whereas most of them are methylated in eukaryotic DNA, which additionally increases their distinctiveness. Non-methylated CpG motifs are non-methylated desoxycytidylate-desoxyguanylate dinucleotides in the prokaryotic genome or in fragments thereof.

The invention is further based on the finding that the protein according to the invention specifically binds to non-methylated CpG motifs. This specific binding property of the protein according to the invention is utilized in order to bind prokaryotic DNA and thus to subsequently enrich, separate and isolate it from a sample, e.g. with a majority of eukaryotic DNA.

The term "DNA containing non-methylated CpG motifs" refers to both eukaryotic and prokaryotic DNA. Said DNA can be purified and dissolved again (e.g. non-methylated DNA isolated from tissues) or be present directly in the original source (e.g. body fluid, such as blood, serum, tracheal aspirate, urine, bronchoalveolar lavage, nose smear, skin smear, puncture fluid).

According to a preferred embodiment, the DNA containing non-methylated CpG motifs is prokaryotic DNA, in particular bacterial DNA.

The term "homology" in the sense of the present invention relates to the degree of identity of two protein sequences. For example, a homology of 60% means that 60 out of 100 amino acid positions in the sequences are identical. The term "shortened" used in order to characterize the protein according to the invention means that the length of the amino acid sequence of the protein according to the invention (e.g. CPGbP181) is shorter than the length of the amino acid sequence of the wild type CGBP protein (CPGbP656). Shortening is effected at the N-terminus and at the C-terminus of the wild type protein sequence (FIG. 1). The maximum shortening is represented by the DNA binding site of the protein.

The protein employed according to the invention may have a molecular weight of, for example, approximately 19,959 Dalton (native) or 21,444 Dalton (in plasmid pQE60). In another preferred embodiment the isoelectric point of the protein according to the invention is approximately 10.09 (native protein) or 10.15 (in plasmid pQE60). A particularly preferred protein employed according to the invention has the amino acid sequence shown in SEQ ID No. 2 or in FIG. 1. This protein has particularly good binding properties as compared to non-methylated CpG motifs of prokaryotic DNA.

The protein described in EP 02020904 (CPGbP241), which is a shortened variant of the wild type CGBP protein (CPGbP656) and served as the basis for the protein employed according to the invention (e.g. CPGbP181), has a length of 241 amino acids, a molecular weight of approximately 33,650 Dalton (native) or 28,138 Dalton (in plasmid pQE60) and an isoelectric point of 9.89 (native) or 9.88 (in plasmid pQE60). The cDNA and amino acid sequence is shown in FIGS. 1 and 2.

The wild type CGBP protein has a length of 656 amino acids, 135 positively charged residues and 94 negatively charged residues, a molecular weight of approximately 75,684 Dalton and an isoelectric point of 8.15. The cDNA and amino acid sequence is shown in FIG. 1.

The sequence comparison of the protein CPGbP181 according to SEQ ID No. 2 used according to the invention with the protein described in EP 01010904 (CPGbP241) is shown in FIGS. 1 and 2.

The protein employed according to the invention is preferably produced by cloning the corresponding cDNA sequence into a plasmid and by expression in *Escherichia coli*. An *E.coli* strain expressing the protein according to the invention was deposited with the Deutsche Sammlung für Mikroorganismen und Zellkulturen under No. DSM 16229 on Feb. 16, 2004. Alternatively, other methods of manufacture known in the art can be applied. The use of plasmid pQE9 represents an exemplary possibility, but any other suitable plasmid is useful as a vector. Expression in *E.coli* is also just an example. Expression in other prokaryotic systems and also in a eukaryotic system as well as chemical or enzymatic synthesis or purification from a natural source, such as e.g. tobacco plants, are further possible embodiments of protein extraction. The protein can be produced both on a laboratory scale (e.g. in an Erlenmeyer flask) and on an industrial scale (e.g. fermenter). For example, the protein according to the invention can be purified by binding histidine residues (His-tag), which are introduced at the beginning or at the end of the protein, to a suitable nickel-containing matrix, which is a method known in the art.

Further possibilities of purification may be any type of fusion proteins allowing purification via suitable matrices (columns, gels, beads etc.). Other forms of tags may be fusion peptides/fusion proteins, e.g. streptavidin-tag, Myc-tag and others.

A preferred form of the protein used according to the invention is the native form, but a denatured form is also suitable for binding non-methylated CpG motifs. "Denaturated forms" in the sense of the present invention are understood to be secondary structures other than those found in nature.

The native or denaturated form of the protein used according to the invention is an exemplary embodiment. The invention includes in vitro-synthesis as well as any other chemical or enzymatic modifications of the protein, such as e.g. incorporation of disulfide bridges, glycosilations, phosphorylations, acylations, amino acid exchanges as well as fusion with proteins or other molecules. Such modifications may be achieved, for example, by recombination and/or expression and/or chemical and/or enzymatic modification of single or multiple amino acids.

The protein used according to the invention has a multiplicity of advantages. It is better in binding prokaryotic DNA via non-methylated CpG motifs than the wild type CGBP protein or variants thereof with a homology of 80% or more. This makes it possible to specifically separate and/or enrich the prokaryotic DNA of a mixture of prokaryotic and eukaroytic DNA. This ultimately enables quick and simple detection of pathogens as well as early diagnosis of infections which may be caused by bacterial pathogens. Conversely, the invention can also be used for depletion of microbial DNA in the sense of purification in the case of clinical conditions accompanied by non-physiological presence of bacteria or their cleavage products in body fluids, in particular blood, of patients. This applies even more because it is well documented that bacteria and also their cleavage products, such as, for example, bacterial DNA, are responsible for a multiplicity of biological effects detrimental to the patient.

Due to the good binding ability of the protein used according to the invention to non-methylated CpG motifs of prokaryotic DNA, the invention relates to a method of separating and/or enriching prokaryotic DNA, comprising the steps of:
 a) contacting at least one prokaryotic DNA present in solution with a protein which specifically binds prokaryotic DNA and has 25% to 35% homology with the wild type CPGB protein, thus forming a protein-DNA complex, and
 b) separation of said complex.

The DNA can be purified and dissolved again or may be present directly in the original source (e.g. body fluid, such as blood, serum, tracheal aspirate, urine, bronchoalveolar lavage, nose smear, skin smear, puncture fluid).

Separation may be effected by different methods of separating, isolating or enriching DNA protein complexes or DNA polypeptide complexes that are well-known to the person skilled in the art. In doing so, use will be made preferably of methods in which the DNA-binding protein is or is being immobilized to a carrier in order to separate and/or enrich the DNA from the sample solution.

According to a preferred embodiment, separation is followed by a step of separating the DNA from the protein according to the invention in said complex. This may be effected, for example, by conventional methods of DNA purification known to the person skilled in the art. In the most simple case, separation is effected by changing the pH value or the salt concentration (e.g. to 1 M NaCl) of the medium/buffer or by adding chaotropic reagents, etc.; i.e. suitable parameters which lead to the separation of the protein-DNA-complex. Such methods are known to the person skilled in the art.

According to a further preferred embodiment, the protein according to the invention is coupled to a carrier. This embodiment represents a particularly simple way of enriching prokaryotic DNA, because separation from the solution is particularly easy, for example by means of physical removal (e.g. by centrifugation) of the charged carrier(s) from the solution.

For the solution of the prokaryotic DNA, any suitable solvent is basically contemplated. However, the method is particularly useful for enriching prokaryotic DNA from solutions which contain different biomolecular species, in particular different types of DNA. The invention preferably relates to a method of separating and enriching prokaryotic or viral DNA from a mixture of prokaryotic and eukaryotic DNA. In doing so, for example, the prokaryotic DNA which is present in body fluids is separated from the eukaryotic DNA by specific binding to the protein according to the invention and is enriched. The prokaryotic DNA enriched in this way facilitates detection of prokaryotic pathogens with the help of molecular biology methods and can contribute to the diagnosis of diseases caused by pathogenic pathogens.

In particular, the embodiment according to which the DNA-binding protein is immobilized to the surface of a carrier is suitable for adsorption of prokaryotic DNA from body fluids, preferably from blood. Moreover, this approach allows removal of microbial DNA, which is present in blood or other body fluids, from said fluids. The body fluid (e.g. whole blood, serum or liquor) purified in this way from the microbial DNA which is also capable by itself to initiate severe inflammatory reactions in patients, can then be fed back into the body. This principle may also be used for depletion of prokaryotic DNA from physiological fluids in the sense of purification, utilizing the specific binding properties of the protein according to the invention.

In order to increase the binding capacity and binding efficiency with respect to non-methylated CpG motifs of DNA, the invention provides a method enhancing the binding capacity and binding efficiency of the protein and thus allowing improved separation and/or enrichment of non-methylated DNA from a mixture of methylated DNA and non-methylated DNA.

According to the invention, this is achieved by indirect coupling of the protein to the matrix. This method will be described hereinafter with reference to FIGS. 9 and 10.

In order to enhance the binding capacity and binding efficiency of the CpGbP-181 protein with respect to DNA containing non-methylated CpG motifs, the invention relates to indirect binding of the protein to the matrix via a spacer. By coupling the protein to the matrix via a spacer, the degree of mobility as well as the number of free binding sites of the CpGbP-181 protein is increased. Thus, increased binding capacity and binding efficiency are achieved. This further allows to reduce the amount of protein used.

Spacers in the sense of this invention are understood to be short chain-like molecules, which allow a spatial distance between the matrix and the protein used according to the invention, e.g. the CpGbP-181 protein. Such spacers are known in the art, e.g. from affinity chromatography or immobilization of proteins. Such chain-like molecules are composed of C and H atoms as well as optionally hetero atoms, e.g. N. These chain-like molecules are made up of individual chain members on the basis of the C atoms, e.g. $CH_2$, and potentially present hetero atoms, e.g. NH. In particular, the spacer comprises 4 to 20, preferably 7 to 10 chain members. A particularly preferred spacer is derived from diamine hexane ($NH_2(CH_2)_6$—$NH_2$). Antibodies in the sense of the present invention are not to be considered as spacers.

A matrix in the sense of this invention relates to substances which function as carriers for the spacer and the protein. Carrier materials may be, for example, sepharose, pearl cellulose, silica, or similar substances known in the art.

Body fluids in the sense of the invention are understood to be all fluids originating from the body of a mammal, including humans, in particular such fluids in which disease pathogens may occur, such as blood, urine, liquor, pleural liquids, pericardial liquids, peritoneal liquids as well as synovial liquids. The description of the invention referring to human blood is not to be construed as limitative, but only as an exemplary application.

Bacterial pathogens are preferably understood to be pathogens of sepsis, but also any other bacterial pathogens of infections. They may differ from commensal pathogens, which are part of the normal population of the organism and are sometimes also found in test samples from patients, but do not have any clinical significance.

When isolating total DNA from infected body liquids, the ratio of host-DNA to pathogen-DNA may be, in many cases, only $1:10^{-6}$ to $1:10^{-8}$ or even less. Through the specific binding of prokaryotic DNA to the protein according to the invention, the method according to the invention enables enrichment by 1 exponential unit and more.

The protein used according to the invention may be coupled directly or indirectly to the carrier. The type of coupling depends on the carrier and the carrier material. Suitable carriers include, in particular, membranes, microparticles and resins, or similar materials for affinity matrices. Suitable materials for binding the protein according to the invention, as well as—depending on the type of material—for carrying out such binding are well-known to the person skilled in the art. For indirect coupling, specific antibodies against the protein according to the invention or the polypeptide are suitable, for example, which are in turn bound to the carrier by known methods.

One application of the method according to the invention consists in enriching prokaryotic DNA. A further application consists in the separation of prokaryotic DNA from a mixture of eukaryotic and prokaryotic DNA by binding the prokaryotic DNA to the protein used according to the invention, which has been immobilized, for example, to a matrix. The mixture of the body's own DNA and prokaryotic DNA is contacted with the affinity matrix by means of suitable methods and, in doing so, the prokaryotic DNA is bound to the immobilized protein; the eukaryotic DNA passes, for example, through a separating column and may be collected separately. Affinity matrices may be, for example, polymeric polysaccharides, such as agaroses, other biopolymers, synthetic polymers, or carriers having a silicate backbone, such as porous glasses or other solid or flexible carriers on which the DNA-binding protein used according to the invention is immobilized. After separation of prokaryotic DNA from eukaryotic DNA has been effected, the affinity matrix is rinsed with a suitable reagent, so that the binding protein with the coupled prokaryotic DNA is separated from the matrix and/or the prokaryotic DNA is separated from the binding protein and is available in a sufficient amount for further process steps.

A further application of the method according to the invention consists in the separation and enrichment of prokaryotic DNA from eukaryotic DNA by binding the prokaryotic DNA to the protein according to the invention, which has been immobilized on microparticles. In this connection, all microparticles which allow the DNA-binding protein according to the invention to be immobilized are suitable. Such microparticles may consist of latex, plastics (e.g. styrofoam, polymer), metal, or ferromagnetic substances. Furthermore, use may also be made of fluorescent microparticles, such as those available from the Luminex company for example. After the prokaryotic DNA has been bound to the proteins used according to the invention, which are immobilized on microparticles, said microparticles are separated from the mixture of substances by suitable methods, such as filtration, centrifugation, precipitation, sorting by measuring the intensity of fluorescence, or by magnetic methods. After separation from the microparticles, the prokaryotic DNA is available for further processing.

Another application of the method according to the invention consists in the separation and enrichment of prokaryotic DNA from eukaryotic DNA by binding the prokaryotic DNA to the protein used according to the invention, which is subsequently separated from other ingredients of the mixture by electrophoresis.

A further application of the method according to the invention consists in the separation and enrichment of prokaryotic DNA from eukaryotic DNA by binding the prokaryotic DNA to the protein used according to the invention. The protein used according to the invention is subsequently bound to corresponding antibodies. The antibodies may be bound to solid or flexible substrates, such as glass, plastics, silicone, microparticles, membranes, or may be present in solution.

After binding of the prokaryotic DNA to the protein according to the invention and binding of the latter to the specific antibody, separation from the substance mixture is effected by methods known to the person skilled in the art.

The method according to the invention may also be used in order to purify body fluids to remove prokaryotic DNA therefrom. In this connection, it is convenient for separation to be effected extra corporally, under sterile conditions, to allow the body fluids to be fed back into the body again, so that the body's own immune system is assisted in eliminating infections by removing the prokaryotic DNA contained in said body fluid.

Any suitable chemical, mechanical or electrochemical processes may be considered for extracorporal removal of prokaryotic DNA from body fluids. Further, the combination with other extracorporal methods, such as hemoperfusion, heart-lung machine or endotoxin adsorbers, is a further convenient application.

The protein used according to the invention can also be used to detect prokaryotic DNA. In this case, enrichment of the prokaryotic DNA is followed by a step of amplifying said prokaryotic DNA, for which all common methods of amplification are suitable (PCR, LCR; LM-PCR, etc.).

The method according to the invention, in particular with the above-described embodiments, has the advantage that, by specific binding of non-methylated prokaryotic DNA, rich in CpG motifs to proteins with specific affinity for such structures, prokaryotic DNA from the total DNA of an infected host is successfully concentrated and thus the sensitivity of detection of pathogen DNA in body fluids is strongly enhanced.

The possibilities of separating prokaryotic DNA from eukaryotic DNA using a specifically binding protein are no more time-consuming than known methods of isolating total DNA. However, subsequent detection can then be effected only by PCR. A nested PCR will not be required in most cases, which makes it possible to save a considerable amount of time in diagnostics.

The use of the protein of the invention to deplete prokaryotic DNA in physiological body fluids was already mentioned above. Depletion in the sense of the present invention means that the amount of prokaryotic DNA is reduced. This possibility of reducing prokaryotic DNA also enables the use of the proteins according to the invention in environmental technology, waste water management and air conditioning technology.

The invention further relates to a method of separating and enriching non-methylated genomic DNA from a mixture of non-methylated genomic and methylated genomic DNA. The methylated genomic DNA is separated by binding the non-methylated genomic DNA to the CpGbP-181 protein coupled to a matrix. This procedure contributes substantially to the simplified examination of the methylation patterns of methylated genomic DNA and enables the diagnosis of diseases having a specific methylation pattern.

Moreover, the invention relates to a kit for enriching prokaryotic DNA by one of the above-described methods, said kit containing at least the protein according to the invention, optionally together with further reagents suitable to carry out said method.

In addition to the protein according to the invention, said kit may contain at least one set of primers, which are suitable to amplify genomic DNA of certain prokaryonts under standard conditions.

The invention will be explained in more detail below with reference to the examples, without limiting it thereto.

EXAMPLE 1

Preparation of the Protein According to the Invention

The DNA sequence for the complete CPGbP protein was used to construct primers 1 (GGATC CGGTGGAGGGCGCAAGAGGCCTG-fw SEQ ID No. 3) and 2 (AAGCTTAGAGGTAGGTCCTCAT-CTGAG-rv SEQ ID No. 4) which amplify a shortened DNA fragment encoding CPGbP-181, which is a shortened protein binding CPG. After cleavage, the DNA fragment was ligated into the pQE9 vector (Qiagen) using restriction enzymes BamHI and Hind III. An open reading frame forms in pQE9, in which frame a DNA fragment encoding 6× His-Tag (pQE9[6HisCPGbP181]) is fused to the 5' end. The complete amino acid sequence of the encoding fusion protein 6His-CPGbP181 is shown hereinafter, the portion indicated in bold print representing the peptide CPGbP181 and the portions indicated in italics indicating fused foreign amino acids of plasmid pQE9.

Plasmid pQE9[6HisCPGbP181] was transformed to the E. coli expression strain M15[pREP4] (Qiagen). The clone is referred to hereinafter as M15[pCPGbP181], and the expressed protein is referred to as rCPGbP181. Expression of the protein rCPGbP181 occurred according to the following protocol: A colony of the expression strain M15 [pCPGbP181] is grown overnight in 2 ml Luria Medium with 100 µg/ml ampicilline and 25 µg/ml kanamycine at 37° C. with shaking. Then, the pre-culture is transferred to 200 ml preheated nutrient medium containing the same concentrations of antibiotics. After 3 hours of growth at 37° C. with shaking, IPTG is added to induce expression, and incubation is continued for 5 hours. Thereafter, the bacteria are removed by centrifugation and the sediment is re-suspended in 5 ml 0.2 M tris buffer, pH 7.5. The bacteria are subjected to ultrasonic treatment in an iced bath for 5×1 min. After centrifugation, the sediment is re-suspended in 10 ml 0.2 M tris, 2M urea, pH 7.5, and shaken for 15 min. After centrifugation has been effected, the remaining sediment is taken up in 0.2 M tris, 6M guanidine hydrochloride, 0.001 M dithioeritrite (DTE), 0.02 M imidazole, and suspended therein. The inclusion bodies are dissolved at room temperature for 1 hour with agitation. After centrifugation, the crude protein is present in the supernatant and can be applied directly to a 3 ml Ni-agarose column. The subsequent steps should be effected in the cooling chamber at +4 to +6° C. First, the column is washed with 0.2 M tris, 6M guanidine hydrochloride, 0.001 M dithioeritrite (DTE), 0.02 M imidazole buffer, pH 7.5, until extinction has reached the zero line. From this point, rCPGbP181 can be obtained in different ways: 1. as a denaturated protein, dissolved in 6M guanidine hydrochloride or 6M urea, and 2. as a native protein, soluble in buffers at physiological concentrations. In the second case, however, the yield is lower.

Purification According to Method 1 (Denaturated):

The protein rCPGbP181 is eluted from Ni—NTA agarose with an imidazole gradient of 0-0.5 M, M in buffer 0.2 M tris, 6M guanidine hydrochloride, 0.001 M dithioeritrite (DTE), 0.02 M imidazole, pH 7.5, as the basic material. In doing so, rCPGbP181 is detached from the column at 0.2-0.3 M imidazole. The protein thus obtained is dialyzed against 0.2 M tris, 6M urea, 0.001 M dithioeritrite (DTE), pH 7.5, and frozen. During dialysis against physiological buffers, purified rCPGbP181 is thus precipitated.

Purification According to Method 2 (Native):

According to this method, the guanidine hydrochloride concentration is shifted from 6 mol on Ni—NTA agarose with the bound rCPGbP181 via a gradient up to 0 mol guanidine hydrochloride. The basis for this is the buffer 0.2 M tris, 0.5 M NaCl, 0.001 M dithioeritrite (DTE), 0.02 M imidazole, pH 7.5. In this case, a flow rate of 0.5 ml/min was selected. Subsequently, an imidazole gradient of 0 to 0.5 mol was applied for elution in buffer 0.2 M tris, 0.5 M NaCl, 0.001 M dithioeritrite (DTE), pH 7.5, as basic material. In this case, too, a substantial proportion of the bound protein (20%) was eluted at 0.2 to 0.3 mol imidazole. This native rCPGbP181 eluate remained dissolved in this buffer even after dialysis in PBS. However, it is disadvantageous that approximately 80% of rCPGbP181 bound to Ni—NTA agarose remained on the column under these conditions and were subsequently extractable only under the denaturated conditions of method 1. This means that the yield of method 2 as used resulted only in 20% native rCPGbP181 soluble in physiological buffers.

EXAMPLE 2

Detection of Pathogens by Means of Nested PCR

Fresh, heparinized human blood, which contains streptococcus pyogenes with $10^3$/ml colony-forming units as pathogens, is used for detection of pathogens. The DNA is isolated by means of absorption to DNA-binding matrix using commercial kits for isolation of total DNA from body fluids according to modified instructions from the manufacturers. For this purpose, 200 µl of the total lysis buffer, which contains proteinase K and SDS, is added to 100 µl of infected blood in Eppendorf tubes. The mixture is incubated at 37° C. for 30 min and then heated to 95° C. for 20 min. After cooling, 20 µg of mutanolysine are added and incubated at 37° C. for another 60 min. After centrifugation, the mixture is applied to the centrifugation columns using DNA-binding matrix and the DNA is purified according to manufacturer's instructions. The purified DNA is placed in a final volume of 100 µl of 0.01 mol tris buffer, pH 7.5, or in an equal amount of elution buffer from the manufacturer. For detection of pathogens, primers were selected to identify the streptolysin O gene (slo).

1. PCR. Amplification of a 465 bp fragment

```
                                      (SEQ. ID No: 5)
Forward primer 1:   5'-AGCATACAAGCAAATTTTTTACACCG (SEQ. ID No: 6)
Reverse primer 2:   5'-GTTCTGTTATTGACACCCGCAATT
```

Primer concentration 1 mg/ml
Starting material: 5 µl isolated DNA
0.5 µl primer fw 1
0.5 µl primer rv 2
14 µl aqua dest
total 25 µl in Ready to go Kit (Amersham-Pharmacia)
Reaction:
5 min 95° C.
40 cycles (30 sec. 95° C.; 30 sec. 51° C.; 3 min 72° C.; 1×7 min 72° C.).

The first PCR of streptococci-DNA in human blood is shown in FIG. 1 (10 µl each of the 25 µl starting material were separated. 1) PCR starting material containing 5 µl template DNA; 2) starting material containing 5 µl template, at a dilution of 1:10. 3) positive control: 0.2 µl of streptococci-DNA as template in the absence of eucaryotic DNA from blood. ST) molecular weight standard)

Result: The first primary PCR does not result in a positive reaction. Therefore, a second PCR (nested PCR) was subsequently carried out.

2. PCR (Nested): Amplification of a 348 bp Fragment in the above slo-fragment.

Forward primer 3: 5'-CCTTCCTAATAATCCTGCGGATGT (SEQ. ID No: 7)

Reverse primer 4: 5'-CTGAAGGTAGCATTAG TCTTTGATAACG (SEQ. ID No: 8)

Primer concentration: 1 mg/ml
Starting material: 5 µl from PCR1, sample 1, FIG. 1
0.5 µl primer fw 1
0.5 µl primer rv 2
14 µl aqua dest
total 25 µl in Ready to go Kit (Amersham-Pharmacia)
Reaction:
5 min 95° C.
40 cycles (30 sec. 95° C.; 30 sec. 54° C.; 3 min 72° C.; 1×7 min 72° C.)

Figure 4:
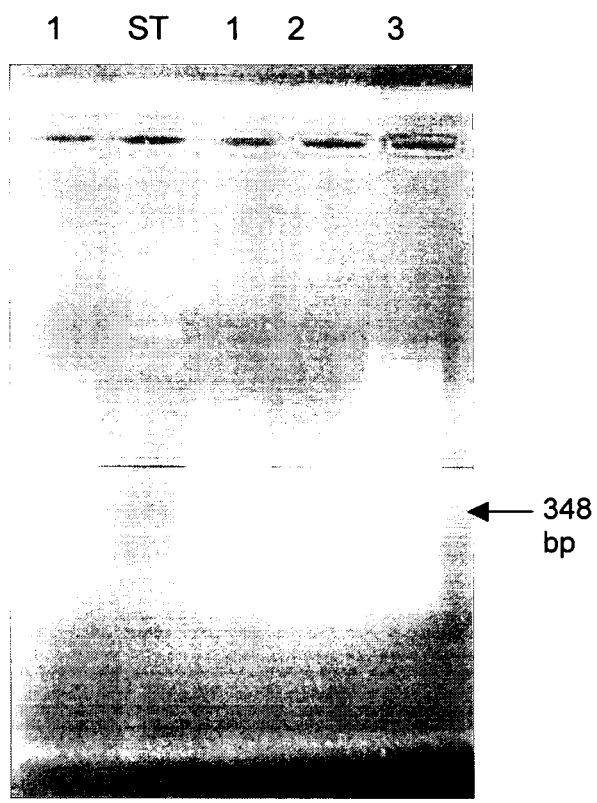
FIG. 4 shows a nested PCR with the PCR products from the primary PCR approach of FIG. 3 as template.

FIG. 4 shows the nested PCR with the PCR products from the primary PCR starting material according to FIG. 3 as template. The samples correspond to those of FIG. 3.

Result: In the nested PCR, the desired slo-DNA fragment is amplified at a concentration of 100 streptococci cells per 100 µl blood (sample 1). For 5 µl starting material in the 1$^{st}$ PCR (FIG. 3), this corresponds to about 5 to 10 templates. At a dilution of 1:10 (sample 2), sensitivity is exhausted (0.5 to 1 template).

These experiments show that successful PCR detection of pathogens in blood requires isolation of the total DNA from at least 1 to 5 ml blood. However, the total DNA concentration is then too large to be used directly in a PCR.

Other pathogen-specific nucleic acid detections without an amplification step by direct detection of the bacterial DNA, for example by DNA hybridization, are also too insensitive, which is primarily due to the high excess of human DNA relative to bacterial DNA. In addition, competitive processes during DNA analysis as well as the low quantity of bacterial DNA are to be regarded as hindrances to qualitative and quantitative analysis. The common methods of DNA isolation enrich the total DNA of a body fluid so that the ratio of host DNA to microbial DNA can be between $1:10^{-6}$ and $1:10^{-8}$. This difference makes it easy to understand the difficulty in detecting microbial DNA in body fluids.

EXAMPLE 3

Determining the Binding Properties of rCPGbP181

Figure 5:
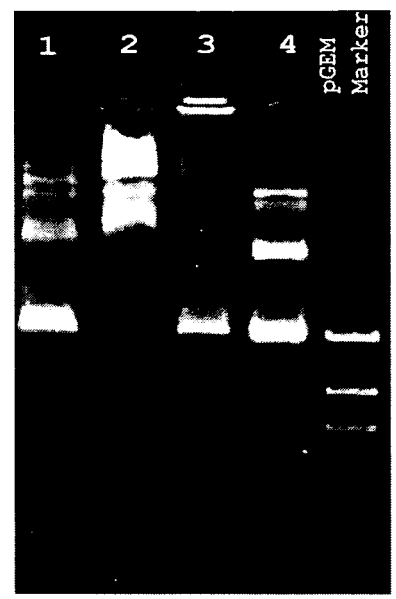
FIG. 5 shows a gel retardation experiment.
Figure 6:
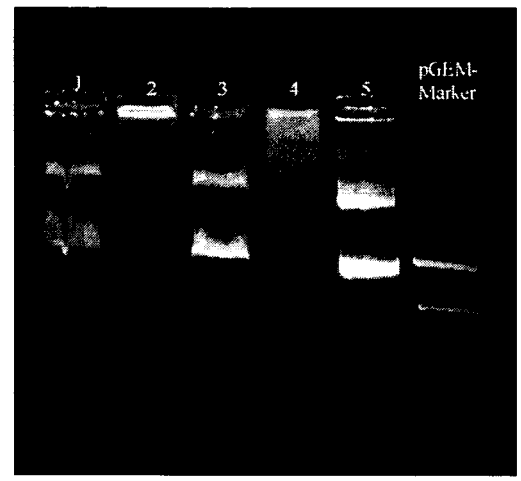
FIG. 6 shows a further gel-retarding experiment.

In gel retardation experiments both the binding of the denaturated and of the native protein rCpGbP181 to methylated and to non-methylated DNA molecules with CpG motifs was examined. The pUC18 plasmid of *E. coli* was used as the test DNA with an inserted M-protein gene segment of *streptococcus dysgalactiae* supsp. *equisimilis* (Geyer et. al FEMS Immuno. Med. Microbiol. 26:11-24, 1999). The plasmid preparation was divided and one half was methylated with the CpG methylase kit of New England BioLabs. Both preparations were mixed with rCPGbP181 (native or denaturated) and electrophoretically separated on agarose gel. The results are shown in FIGS. 5 and 6. Both the native form and the denaturated form of rCPGbP181 showed a higher affinity to non-methylated plasmid DNA, which confirms the selective binding property with respect to non-methylated CpG-rich DNA.

Description of the gel retardation experiment according to FIG. 5: 5 µl (72 ng) methylated pUC18emm DNA and 1 µl (142 ng) non-methylated pUC18emm DNA, respectively, were mixed with 5 µl (0.5 µg) native rCPGbP181 and filled up to a volume of 35 µl with the following buffer: 0.01 M tris, 0.08M NaCl, 0.001M EDTA, 0.005M DTE, 5% glycerine, pH 7.8. After incubation at 20° C. for 30 min the mixtures were electrophoretically separated on 1.5% agarose. Methylated DNA was applied in lanes 1 and 3 and non-methylated DNA was applied in lanes 2 and 4. In lanes 1 and 2 the DNA was mixed with native rCPGbP181. Lane 2 shows that non-methylated pUC18emm interacts with rCPGbp181; in contrast thereto, rCPGbP181 did not show any interaction with methylated pUC18emm (lane 1). Lanes 4 and 5 are the plasmids without addition of rCPGbP181 as controls.

Description of the gel retardation experiment of FIG. 6 for non-methylated and methylated pUC18emm after incubation with denaturated rCPGbP181. The concentrations correspond to those of FIG. 5. Methylated DNA was applied in lanes 1 and 3 and non-methylated DNA was applied in lanes 2 and 4. In lanes 1 to 4, the DNA was mixed with two different batches of denaturated rCPGbP181. Lanes 2 and 4 show that non-methylated pUC18emm also interact with denaturated rCPGbP181; however, rCPGbP181 did not show any interaction with methylated pUC18emm (lanes 1 and 3). Lane 5 is pUC18emm without rCPGbP181 as control.

EXAMPLE 4

Binding and Separation of a Mixture of Calf Thymus DNA and Bacterial DNA to Immobilized CPGbp181

Purified CPGbp181 was coupled to aminohexyl sepharose (Amersham-Biosciences) by means of glutaraldehyde according to the protocol of Cambiasso et al. (Cambiasso, C. et al., Immunochemistry 12-273-278, 1975). The concentration of immobilized protein was 0.3 mg per milliliter sepharose. 300 µl sepharose was placed in a spin-filter tube containing inert fritting material which absorbs neither DNA nor protein, but retains sepharose.

Figure 7:
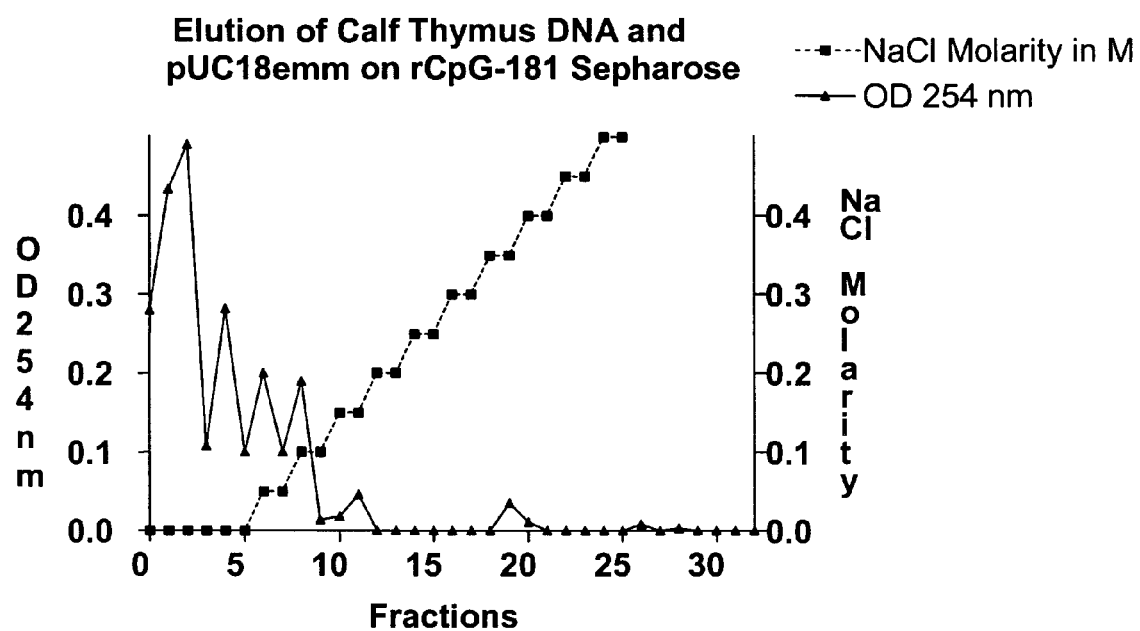
FIG. 7 shows the elution of calf thymus DNA and pUC18emm by rCpG-181 sepharose.
Figure 8:
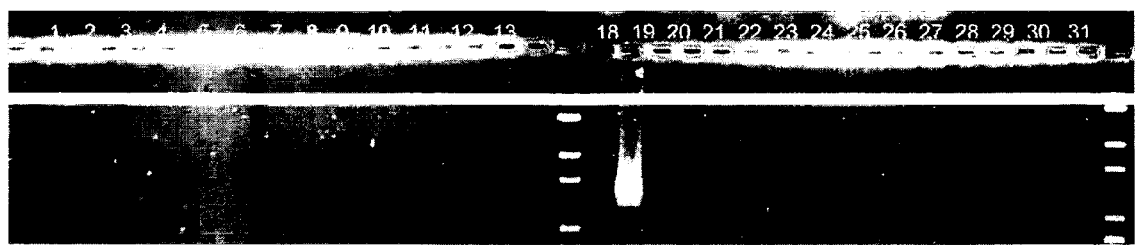
FIG. 8 shows the determination of the eluted DNA in the fractions by measurement of the extinction at 254 nm as a function of the NaCl gradient.

200 ng calf thymus DNA and 25 ng pUC18emm was dissolved in 100 µl to 20 mM tris-HCL buffer, pH 7.5, and applied to the column thus prepared. After each step, the liquid was centrifuged at 14,000 RPM for 0.5 min in an Eppendorf centrifuge in one fresh Eppendorf tube each. Thus, a two-step increase of the NaCl concentration was effected from 0 to 1M. DNA precipitation was effected in each tube by adding 10 µl 4 M acetate, ph 4.5, and 250 µl ethanol abs., mixing and centrifugation at 14,000 RPM for 15 min. Thereafter, the supernatant was discarded and the precipitate was washed with 300 µl 70% ethanol. After discarding, the residue was dried for 5 min in a vacuum centrifuge and then taken up in 15 1 distilled water (PCR-suitable). On the one hand, extinction at 254 nm was measured for 10 µl each of the samples (FIG. 7). On the other hand, PCR was effected with sequence primers for PUC18, using 3 µl of each sample (FIG. 8).

The result (FIGS. 7, 8) shows that the eukaryotic calf thymus DNA is initially washed from the column between 0 to 0.1 M NaCl, while the prokaryotic DNA (pUC18emm) was eluted in the fraction at 0.3 M NaCl. This shows that eukaryotic DNA has a lower affinity to CPGbP181 and, thus, a clear separation of both DNA fractions was achieved.

EXAMPLE 5

Enhancement of Binding Properties of the CpG-bP-181 Protein, which Result from Indirect Binding of this Protein to a Matrix Via a Spacer In order to examine binding properties, prokaryotic DNA from a DNA mixture of *staphylococcus aureus* and human DNA was enriched using the directly coupled CpGbP-181 protein on CNBr sepharose or using the indirectly coupled CpGbP-181 protein on sepharose (in the following AH sepharose) via a diaminohexyl spacer (AH).

First, the AH sepharose was incubated at room temperature for 15 min with addition of glutaraldehyde. Next, the AH sepharose was washed with 0.1 mol $Na_2HPO_4$. Then, 0.24 mg of the CpGbP-181 protein was placed on the matrix. The binding of the CpGbP-181 protein to AH sepharose was achieved by incubation at room temperature for 2 hours. The excess CpGbP-181 protein was removed.

After subsequent washing of the CpGbP-181-AH sepharose with 0.1 mol $Na_2HPO_4$ and addition of 0.1 mol glycine, the CpGbP-181-AH sepharose was incubated at room temperature for 2 hours in order to saturate free binding sites. Then, the CpGbP-181-AH sepharose was again washed with 0.1 mol $Na_2HPO_4$. In order to reduce the Schiff base and in order to stabilize binding, the CpGbP-181-AH sepharose was admixed with sodium borohydride and incubated at room temperature for 1 hour.

Next, the CpGbP-181-AH sepharose was washed with 0.1 mol $Na_2HPO_4$.

The storability of the CpGbP-181-AH sepharose at 4° C. is achieved by addition of 20% ethanol. Next, the CpGbP-181-AH sepharose was portioned into columns. The columns prepared with CpGbP-181-AH sepharose were then washed with tris buffer and were available for separation/enrichment of DNA containing non-methylated CpG motifs.

2) Enrichment of the DNA Mixture, Followed by Elution of the Prokaryotic DNA and Determination of the Concentration of Prokaryotic DNA by PCR.

The DNA mixture consisted respectively of 330 ng human DNA and 150 ng prokaryotic DNA (*staphylococcus aureus* DNA). The DNA mixture was placed on the columns prepared with CNBr sepharose or with AH sepharose, respectively, and incubated at room temperature for 1 minute. Then, the columns were centrifuged and washed with 100 l tris buffer (10 µM, pH 7). The washing and centrifugation step was repeated 5 times.

The supernatant was carefully removed and then 100 µl elution buffer (10 µM tris buffer, 0.5 M NaCl, pH 7) each were added to the columns and centrifuged. The elution step was repeated 5 times. Then, the individual fractions of each sample were precipitated by addition of 10 µl 3 M sodium acetate and 250 µl ethanol with subsequent mixing and centrifugation (15 min at 15,000 g). The supernatant was carefully discarded and the pellet was washed with 1 µl ethanol (70%) and centrifuged at 15,000 g. The supernatant was then removed again, the pellet was dried in a vacuum centrifuge and taken up in 30 µl DEPC water. 5 µl each were used for PCR detection.

The PCR used universal primers for the 16 s RNA gene. After carrying out the PCR, 15 µl each of the individual fractions were placed on 2% agarose gel.

Figure 9:
FIG. 9 shows the results of PCR after enrichment of prokaryotic DNA from a DNA mixture of *staphylococcus aureus* and human DNA using coupled CpGbP-181 protein on CNBr sepharose.
Figure 10:
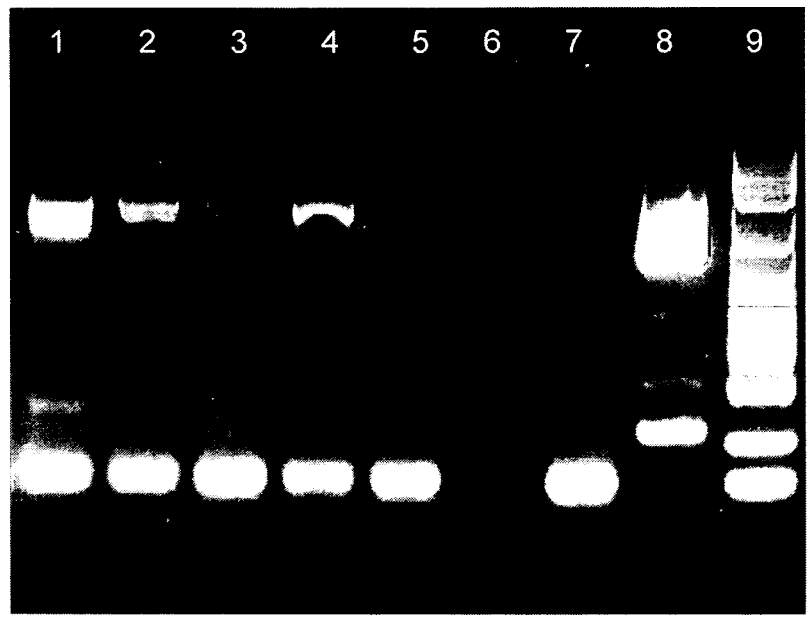
FIG. 10 shows results of PCR after enrichment of prokaryotic DNA from a DNA mixture of *staphylococcus aureus* and human DNA using coupled CpGbP-181 protein on AH-sepharose.

FIG. 9 (direct binding of the CpG-181 protein to CNBr sepharose) and FIG. 10 (indirect binding of the CpG-181 protein to sepharose via a spacer (AH)) show the results of the PCR for the individual fractions. It is clearly evident that the use of the AH spacer allowed more prokaryotic DNA to be enriched (fraction 1, elution fraction). This characteristic improvement in binding properties is useful in the methods according to the invention.

The invention claimed is:

1. A method of separating and/or enriching prokaryotic DNA in vitro, comprising the steps of:
   a. contacting at least one prokaryotic DNA, present in solution, with a protein which specifically binds prokaryotic DNA and has 25% to 35% homology with the wild type CGBP protein, thereby forming a protein-DNA complex, and
   b. separating said complex.

2. The method according to claim 1, wherein the protein comprises the amino acid sequence of SEQ-ID No. 2.

3. The method according to claim 1, wherein the protein is capable of recognizing non-methylated CpG motifs.

4. The method according to claim 1, wherein separation is followed by a step for separating the DNA from the protein of the complex.

5. The method according to claim 1, wherein the protein is bound to a carrier.

6. The method according to claim 5, wherein the protein is bound directly to the carrier.

7. The method according to claim 5, wherein the protein is bound to the carrier via an antibody directed against it.

8. The method according to claim 5, wherein the protein is bound to the carrier via a spacer.

9. The method according to claim 8, wherein a diamino hexane residue is used as the spacer.

10. The method according to claim 5, wherein the carrier is provided as a matrix, as microparticles or as a membrane.

11. The method according to claim 10, wherein sepharose is used as the matrix.

12. The method according to claim 1, wherein separation is effected by means of an antibody or antiserum directed against the protein.

13. The method according to claim 1, wherein separation is effected by means of electrophoresis.

14. The method according to claim 6, wherein the protein is an antibody or a corresponding antiserum directed against non-methylated CpG motifs.

15. The method according to claim 1, wherein the solution contains a mixture of eukaryotic and prokaryotic DNA.

16. The method according to claim 15, wherein the prokaryotic DNA is bacterial DNA.

17. The method according to claim 15, wherein the solution is a body fluid or is derived therefrom.

18. The method according to claim 15, wherein separation is achieved by means of a filter which filters the corresponding DNA-protein complexes.

19. The method according to claim 18, wherein the protein is immobilized to a filter matrix.

20. The method according to claim 1, wherein after step b) the prokaryotic DNA is amplified in a step c).

21. The method according to claim 20, further comprising the steps of:
   a) isolating the prokaryotic DNA from the protein-DNA complex,
   b) denaturating the double-stranded DNA,
   c) hybridising the individual strands of the DNA with complementary primers,
   d) generating double-strand fragments via reaction with polymerases and
   e) repeating these steps up to the desired degree of amplification.

22. The method according to claim 21, further comprising the steps of:
   a) cloning the isolated prokaryotic DNA sequences into vectors,
   b) transforming suitable host cells with these vectors,
   c) cultivating these transformed cells,
   d) isolating the vectors from these cells and
   e) isolating the DNA.

23. The method according to claim 17, wherein the body fluid is full blood, serum, plasma, cell preparations from full blood, urine, liquor, pleural liquid, pericardial liquid, peritoneal liquid, synovial liquid or bronchoalveolar lavage.

24. A method of separating and/or enriching non-methylated DNA from a mixture of non-methylated and methylated DNA in vitro, comprising:
   providing a mixture containing at least one non-methylated DNA and at least one methylated DNA;
   contacting said mixture in a solution with a protein having between about 25% and 35% homology with a wild type CGBP protein to specifically bind said protein and said at least one non-methylated DNA, thereby forming a protein-DNA complex; and
   separating said complex;
   wherein said protein does not specifically bind to said at least one methylated DNA.

25. The method according to claim 24, wherein said method includes a diagnosis of diseases having a specific methylation pattern.

26. The method of claim 25, wherein said specific methylation pattern indicates the presence of cancer.

* * * * *